US008649605B2

(12) United States Patent
Franz et al.

(10) Patent No.: US 8,649,605 B2
(45) Date of Patent: Feb. 11, 2014

(54) METHOD AND APPARATUS FOR DETECTING FOAM ON A LIQUID SURFACE IN A VESSEL

(71) Applicant: Roche Diagnostics Operations, Inc., Indianapolis, IN (US)

(72) Inventors: Tobias Franz, Munich (DE); Martin Gutekunst, Eberfing (DE); Hans-Joachim Polland, Wolfratshausen (DE); Claudia Schiller, Gauting (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/888,567

(22) Filed: May 7, 2013

(65) Prior Publication Data
US 2013/0315486 A1 Nov. 28, 2013

Related U.S. Application Data

(63) Continuation of application No. PCT/EP2011/070250, filed on Nov. 16, 2011.

(30) Foreign Application Priority Data

Nov. 16, 2010 (EP) .................. 10191353

(51) Int. Cl.
G06K 9/46 (2006.01)
(52) U.S. Cl.
USPC .......................................... 382/190
(58) Field of Classification Search
None
See application file for complete search history.

(56) References Cited

U.S. PATENT DOCUMENTS 5,414,778 A 5/1995 Schwartz et al.
2008/0305012 A1 12/2008 Camenisch

FOREIGN PATENT DOCUMENTS

| DE | 4242927 A1 | 6/1994 |
| DE | 202007012346 U1 | 9/2007 |
| DE | 102008023047 A1 | 11/2009 |
| DE | 102010013410 A1 | 8/2010 |
| EP | 1562027 A1 | 8/2005 |
| WO | 00/42384 A1 | 7/2000 |
| WO | 2004/077008 A2 | 9/2004 |
| WO | 2005/003758 A1 | 1/2005 |

OTHER PUBLICATIONS

Guillerme, C. et al., "Study of Foam Stability by Video Image Analysis: Relationship with the Quantity of Liquid in the Foams," Journal of Texture Studies, 1993, pp. 287-302, vol. 24.

Primary Examiner — Stephen R Koziol
Assistant Examiner — Amandeep Saini
(74) Attorney, Agent, or Firm — Roche Diagnostics Operations, Inc.

(57) ABSTRACT

An apparatus and method for detecting foam on a liquid surface in a vessel is presented. The vessel has an upper opening surrounded by a border. The vessel can be a tube-shaped. At least one image is taken from a region suspected to contain foam in the vessel by using an image sensing device that provides corresponding image data. An automatic evaluation of the image is performed on the basis of the image data by a data processing system using an image evaluation program. The at least one image is taken from the top of the vessel through the open upper opening onto the liquid surface. The image evaluation program of the data processing system identifies foam areas and non-foam areas in the image and provides information about the presence or absence of foam areas in the image as a result of the image evaluation.

17 Claims, 11 Drawing Sheets

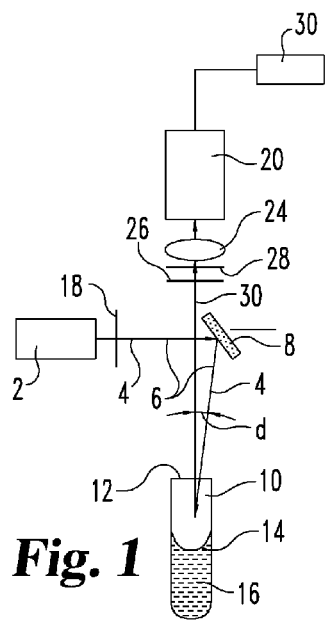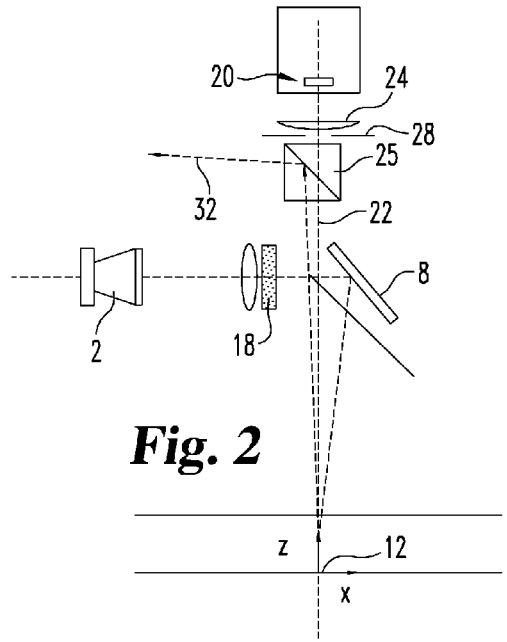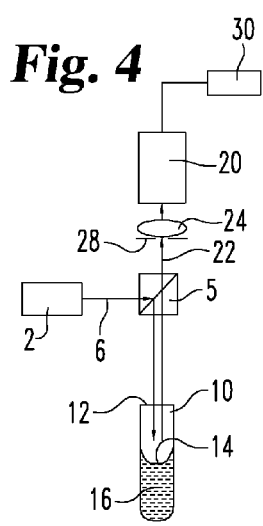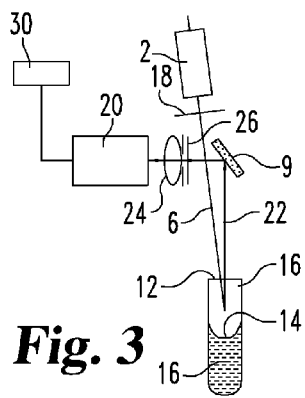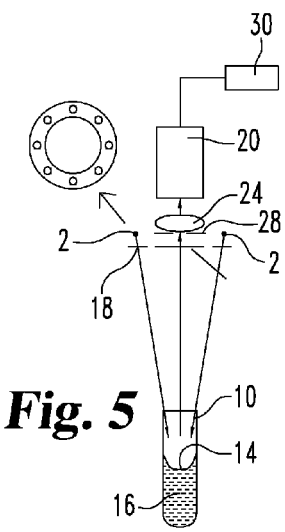

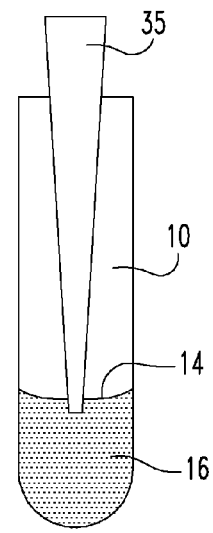 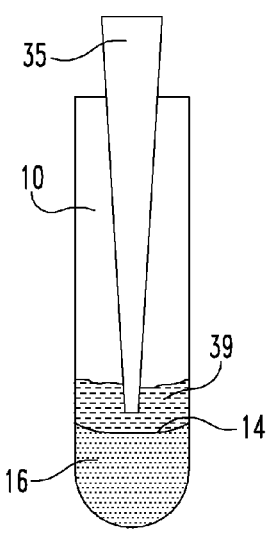 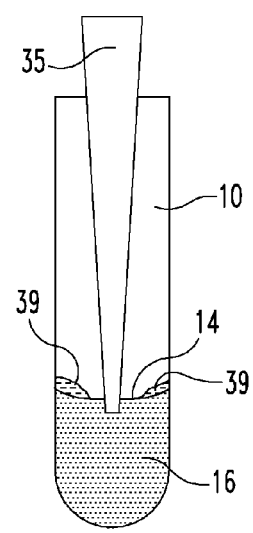
Fig. 6a  Fig. 7a  Fig. 8a
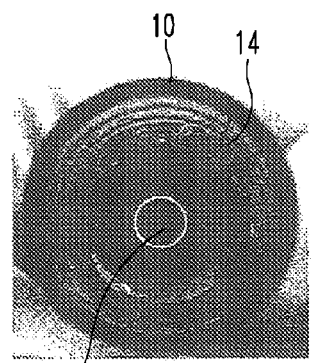 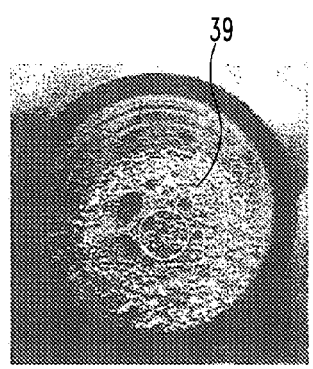 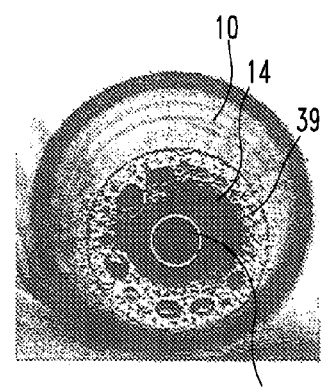
Fig. 6b  Fig. 7b  Fig. 8b

Count: 208   Min:0
Mean: 35.953   Max:77
Std.Dev. 19.263   Mode:31 (1,0)

Count: 208   Min:0
Mean: 5.861   Max:14
Std.Dev. 3.115   Mode:5 (29)

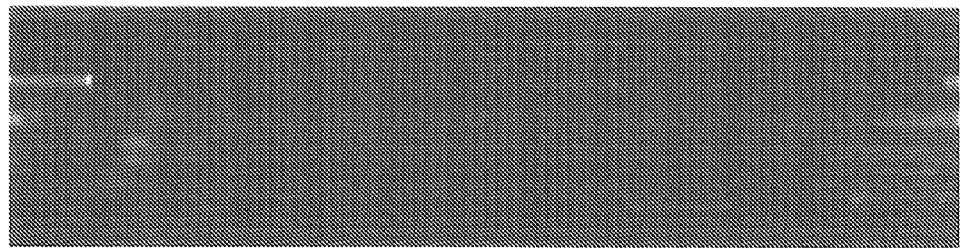
Fig. 23
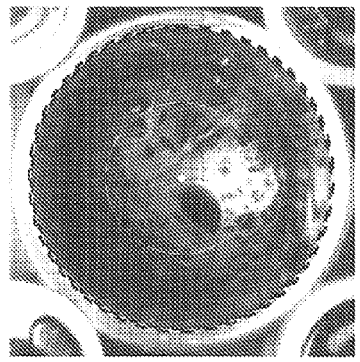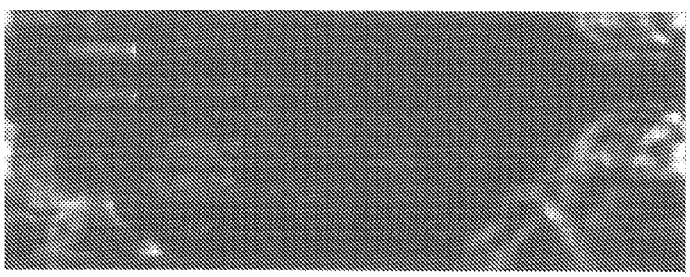
Fig. 24

METHOD AND APPARATUS FOR DETECTING FOAM ON A LIQUID SURFACE IN A VESSEL

CROSS-REFERENCE TO RELATED APPLICATIONS

This application is a continuation of PCT/EP2011/070250, filed Nov. 16, 2011, which is based on and claims priority to EP 10191353.1, filed Nov. 16, 2010, which is hereby incorporated by reference.

BACKGROUND

The present disclosure relates to a method and an apparatus for detecting foam on a liquid surface in a vessel.

Such systems for detecting foam on a liquid surface in a vessel are particularly useful in the field of automatic analysers which comprise pipetting systems for the exchange of predetermined amounts of liquid between vessels, or containers, which are automatically handled in such automatic analyser systems. The pipetting of a liquid sample, or an analyte, from a respective vessel is carried out by a pipette which is slightly immersed with its pipette tip into the liquid, and a predefined volume of the liquid is sucked into the pipette. If there is a foam layer on the liquid, it might happen that the end position of the tip of the pipette is inside the foam layer, and thus a considerable amount of foam will be sucked into the pipette during the pipetting period. This can lead to a wrong analytical result of the automatic analyser.

Since the filling level of the liquid generally changes from vessel to vessel, technical solutions have been already developed to detect the liquid surface level. A collimated light is directed to the surface of the liquid. The preferred incident angle is between 10° and 20°. A semiconductor photo sensor is used as a CCD-photo detector which is directed to the surface of the liquid. Scanning of the incident angle or movement of the complete detection system can give more information about the liquid surface. Air bubbles can be detected by the disturbance of reflectance. The optical detection system can be combined with a capacitance measurement for liquid level detection. The systems of the prior art do not involve image acquisition and image processing for determining the extension of the foam.

A dynamic fluid level and bubble inspection for quality and process control relates to fast image processing for the detection of bubbles in a liquid and gives information on algorithms to characterize the bubbles. However, foam on the surface is not considered and images are taken in transmission and not from the top of the vessel. In a similar, images of foam are taken through the vascular wall of the vessel. There is no description for taking images from the top of the vessel.

Therefore, there is a need to provide an apparatus and method for detecting foam on a liquid surface in a vessel, which can be implemented in an automated liquid pipetting system and which can be executed to automatically distinguish between foam areas and non-foam areas on the liquid surface in a sensitive manner in order to provide information as a basis for the decision whether the vessel is prepared for pipetting liquid therefrom.

SUMMARY

According to the present disclosure, an apparatus and method for detecting foam on a liquid surface in a vessel is presented. The vessel can have an upper opening surrounded by a border. The vessel can be a tube-shaped. At least one image can be taken from a region suspected to contain foam in the vessel by using an image sensing device that can provide corresponding image data. An automatic evaluation of the image can be performed on the basis of the image data by a data processing system using an image evaluation program. The at least one image can be taken from the top of the vessel through the open upper opening onto the liquid surface. The image evaluation program of the data processing system can identify foam areas and non-foam areas in the image and can provide information about the presence or absence of foam areas in the image as a result of the image evaluation.

Accordingly, it is a feature of the embodiments of the present disclosure to to provide an apparatus and method for detecting foam on a liquid surface in a vessel, which can be implemented in an automated liquid pipetting system and which can be executed to automatically distinguish between foam areas and non-foam areas on the liquid surface in a sensitive manner in order to provide information as a basis for the decision whether the vessel is prepared for pipetting liquid therefrom. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 1 illustrates a first embodiment of the apparatus according to an embodiment of the present disclosure.

FIG. 2 illustrates a second embodiment of the apparatus according to an embodiment of the present disclosure.

FIG. 3 illustrates a third embodiment of the apparatus according to an embodiment of the present disclosure.

FIG. 4 illustrates a fourth embodiment of the apparatus according to an embodiment of the present disclosure.

FIG. 5 illustrates a fifth embodiment of the apparatus according to an embodiment of the present disclosure.

FIG. 6a illustrates a schematic diagram of a tube-shaped vessel shown with a liquid with no foam on its upper surface, according to an embodiment of the present disclosure.

FIG. 6b illustrates a photograph of a liquid surface in a vessel with viewing direction from the top of the vessel into the vessel-opening, wherein the liquid surface is substantially free of foam in correspondence with the diagram of FIG. 6a according to an embodiment of the present disclosure.

FIG. 7a illustrates a schematic diagram of a tube-shaped vessel shown with a relatively thick compact foam layer rests on the liquid surface according to an embodiment of the present disclosure.

FIG. 7b illustrates a photograph of a vessel with the same viewing direction as in FIG. 6b, wherein the liquid surface is covered with a foam layer according to the diagram in FIG. 7a according to an embodiment of the present disclosure.

FIG. 8a illustrates a schematic diagram of a tube-shaped vessel with only an outer circular area of the liquid surface covered with foam and the central region greater than the target region for the pipette tip is free of foam according to an embodiment of the present disclosure.

FIG. 8b illustrates a photograph of the tube-shaped vessel with the same viewing direction as FIGS. 6b and 7b, wherein in FIG. 8b the liquid surface has a central region free of foam and a ring-shaped border region covered with foam according to the diagram of FIG. 8a according to an embodiment of the present disclosure.

FIG. 23 illustrates a Fourier transform converted image according to an embodiment of the present disclosure.

FIG. 24 illustrates a foam image (left) with the radial Fourier transformed image (right) according to an embodiment of the present disclosure.

DETAILED DESCRIPTION

Figure 9:
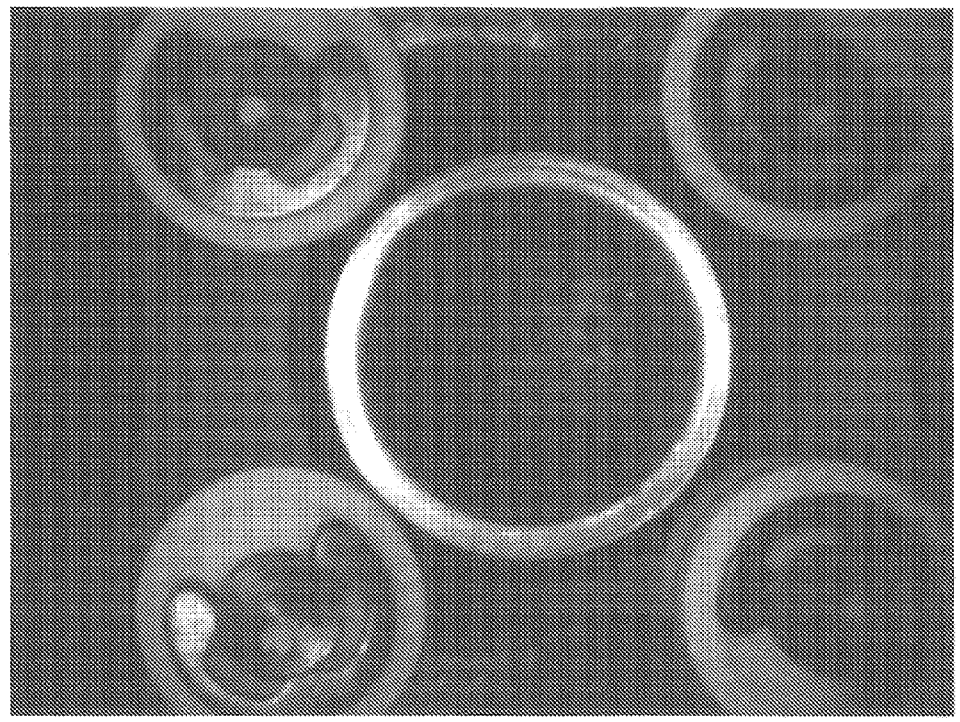
FIG. 9 illustrates an example of an image of foam within a vessel according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The term vessel can denominate a container, such as, for example, a tube, a bottle, a cup and the like. The term tube shaped vessel can denominate a vessel with a substantially cylindrical shape with an open top and a closed bottom.

A method can comprise providing a vessel, such as a tube-shaped vessel, which has an upper opening surrounded by a border and containing an amount of a liquid, taking at least one image from a region suspected to contain foam in the vessel by using an image sensing device providing corresponding image data, and performing an automatic evaluation of the image on the basis of the image data by a data processing system using an image evaluation program. The at least one image is taken from the top of the vessel through the open upper opening onto the liquid surface. The image evaluation program of the data processing system identifies foam areas and non-foam areas in the image and provides information about the presence or absence of foam areas in the image as a result of the image evaluation.

According to the method at least one image of the liquid surface can be taken from the top of the vessel through the open upper opening of the vessel. The observation direction of the image sensing device can correspond substantially to the direction in which a pipette has to be moved with its tip into the respective vessel when liquid is to be pipetted from the vessel. In other words, the image sensing device can be directed to the target area of such a pipette tip and the surrounding of that target area, and this can be an optimal view direction for taking an image of the foam distribution on the liquid surface in the vessel. The image sensing device can be a camera with a CCD-sensor chip or a CMOS-sensor chip which can provide colored or gray-scale images. It may be sufficient to take merely one image of a liquid surface in a particular vessel and to perform the automatic evaluation of the image in order to identify foam areas. The image sensing device may be alternatively operated in a continuous video mode or in a serial mode to provide a series of corresponding images of a liquid surface. The data of corresponding image pixels can be averaged to provide a respective mean value of each pixel for further data processing.

The automatic evaluation of the image can be performed by processing the image data by a data processing system can operate an image evaluation program to identify foam specific areas in the image and to provide information about the presence or absence of foam specific areas in the image as a result of the image evaluation. In one embodiment, the automatic evaluation of the image may provide results of the distribution of foam on the liquid surface in the respective vessel so that a decision can be made whether a sufficient large central region, for example, a target region for pipetting is substantially free of foam. If such a target region of the liquid surface is free of foam, pipetting may be performed regardless of any foam outside that region. The term foam specific area can mean those parts of the image within the vessel border that differ from the homogenous parts of the surface of the liquid.

The image processing or image evaluation can include grabbing the image, identifying the vessel or a specific vessel feature, for example, the border of the open upper opening of the vessel, and identifying or characterising the foam, if present.

There are many conventional image evaluation algorithms the person skilled in the art may choose for identifying typical contours and structures of expected vessel features, foam and non-foam areas in the image. Those image evaluation algorithms may include an algorithm for calculation of a radial image with the image points or pixels are assigned to radial coordinates or polar coordinates. If such a radial image is calculated, a best fit calculation of the vessel opening boarder may be easily performed to a curve which is close to a sine and/or cosine curve, particularly if the border is a circle. After the border is identified, it can be easy to identify the center of the liquid surface and a central target region as seen from above through the opening of the vessel.

For characterisation of the foam, an operator for the detection of edges can be applied to at least part of the image data or to corresponding data derived therefrom, particularly in order to detect borders of foam specific areas in the image. In one embodiment, the well-known Sobel-operator as an operator for the detection of edges can be used. Further, histogram calculation algorithms may be applied for identifying foam specific areas on the liquid surface.

In order to achieve a good quality of the image, the liquid surface may need to be illuminated from the top of the vessel, in one embodiment, and the image may need to be taken through a polarizer in order to suppress light which can be reflected directly from the liquid surface. In one embodiment, the illumination light can be linearly polarized. The polarizer, through which the image is taken, can transmit light that is polarized perpendicular with regard to the polarisation direction of the illumination light.

An apparatus for detecting foam on a liquid surface in a vessel having an upper opening surrounded by a border and containing an amount of a liquid can comprise a holder for positioning a respective liquid containing vessel with its opening at the top at a predetermined location, an illumination device for illuminating the liquid surface in the vessel when the vessel is positioned at the predetermined location, an image sensing device for taking at least one image of the liquid surface from the top of the vessel through the opening of the vessel when the vessel is positioned at the predetermined location and for providing corresponding image data, and a data processing system for performing an automatic evaluation of the image on the basis of the image data and using an image evaluation program that can identify foam specific areas in the image and can provide information about the presence or absence of foam specific areas in the image as a result of the image evaluation. The apparatus can automatically perform the above described method.

The holder for positioning the vessel with its opening at the top at the predetermined location may be a moveable vessel holder of an automatic analyser. An example for such a moveable vessel holder can be a turntable with receptacles for a lot of vessels which can be positioned at predetermined locations by rotating the turntable accordingly.

The illumination device may comprise any type of an adequate light source such as, for example, a LED, light bulb, super luminescence diodes (SLD), laser, arc lamp or a strobe. The wave length of the light emitted by the source can be optimized to the absorption and/or reflection properties of the liquid to be observed. In one embodiment, the illumination device can have a typical wavelength between about 400 nm and about 700 nm, and may use UV-light or infra-red light, if applicable.

The image sensing device may include a CCD-camera or CMOS-camera for taking the images and for providing corresponding image data for the data processing system. The data processing system can be a personal computer or the like.

According to one embodiment, the illumination device can include at least one light source which can illuminate the liquid surface in the vessel either directly or indirectly via a reflecting device from above. Such a reflecting device can be a minor or a beam splitter. In one embodiment, it can be a polarizing beam splitter. In order to achieve a good imaging of the liquid surface, at least one optical imaging lens may need to be arranged in front of the image sensing device. An iris can be positioned in front of the lens in order to achieve a relatively good depth of focus. The iris aperture may be for example about 1 mm.

In one embodiment, a polarizing filter can ben in the illuminating optical path between the light source and the vessel and also a polarizing filter can be in the imaging optical path between the vessel and the image sensing device. The direction of polarization of the polarizing filter in the illuminating optical path can be substantially perpendicular to the direction of polarization of the polarizing filter arranged in the imaging optical path. This arrangement of polarizing filters can be used to suppress light which can be directly reflected from the liquid surface. Alternatively, a polarizing beam splitter may be used instead of two polarizing filters.

In one embodiment, the apparatus may be part of an automatic liquid pipetting system comprising at least one pipette that can operable between the image sensing device and the vessel to suck liquid from the vessel. The automatic liquid pipetting system can have a controller communicating with the data processing system. The controller can control the pipette in dependence of information provided by the data processing system about the presence or absence of foam specific areas in the respective vessel. An automatic liquid pipetting system can include the apparatus.

In another embodiment, the apparatus can be part of an automatic liquid pipetting system which can comprise at least one pipette. The image sensor device can be attached to the pipette or to a moveable holder of the pipette.

Referring initially to FIG. 1, the first embodiment of the apparatus can comprise a light source 2 which can emit a light beam 4 to a mirror 8 along a horizontal part of the illuminating optical path 6. The minor 8 can reflect the light beam 4 downwards under a small angle $\alpha$ with respect to the vertical direction. The reflected light beam can enter a tube-shaped vessel 10 through the ring-shaped upper opening 12. The light beam 4 can illuminate the surface 14 of a liquid 16 in the vessel 10. In the illuminating optical path 6, a polarizing filter 18 can be inserted between the illumination device 2 and the minor 8. The polarizing filter 18 can linearly polarize the light beam 4.

The illumination device 2 can comprise at least one light emitting diode as a light source, but it is to be noted that other kinds of light sources can be applicable. Vertically above the opening 12 of the vessel 10 an image sensing device 20 can be arranged and directed to the vessel 10. In the imaging optical path 22, along which light scattered or reflected from the surface 14 and the surrounding border of the vessel 10 can travel to the image sensing device 20, an optical imaging lens 24 can be in front of the image sensing device 20. In front of the imaging lens 24, a polarizing filter 26 can be in the imaging optical path 22. The direction of polarization of the filter 26 can be substantially perpendicular to the direction of polarization of the filter 18. In order to achieve a great depth of focus, or sharpness, an iris 28 can be in front of the imaging lens 24. The aperture of the iris 28 can be small, in the order of about 1 mm. A data processing system 30, such as, for example, a PC, can be connected to the image sensing device 20 for data transmission. Not shown in the figures is a holder which can position the vessel 10 at the predetermined location beneath the image sensing device 20.

The image sensing device 20 can be a CCD-camera which can provide gray-scale information of images taken therewith, but an image sensing device 20 can be used which can provide color information to be evaluated.

It may not be required that the resolution of the image sensing device 20 be extremely high. Good results can be achieved with a resolution of about 500×500 pixel of a sensor-chip of about 4 mm×4 mm. In one embodiment, shown in FIG. 1 an imaging lens 24 with a focal length of about f=35 mm can be used together with an iris having an aperture of about 1 mm. Since the numerical aperture of the optics can be very small, the depth of sharpness for sufficient optical imaging can extend at least over about +/−40 mm. Such a great range of the depth of focus or sharpness can be important to account for different liquid levels leading to different distances between a respect liquid level 14 in a vessel 10 and the lens 24.

It can be noted that different kinds and shapes of vessels may be employed for exposing a liquid surface to the image sensing device 20. In one embodiment, tube-shaped vessels, for example, standard-tube vessels as shown can be used. The lengths and diameters of the vessels may differ. Good results can be achieved with vessels having a diameter between approximately 5 mm and 20 mm and a length up to about 150 mm. Typical tubes used can have a diameter of about 13 mm and a length of about 100 mm.

The distance between the imaging lens 24 and the highest possible liquid level of a vessel 10 at its predetermined location can be approximately 220 mm and may increase when the liquid level in a vessel 10 is smaller. Such a relatively great distance can allow movement of a pipette between the optical components of the apparatus and the vessel 10 in order to pipette liquid from the vessel 10.

In one embodiment, the apparatus can be integrated in an automatic analyser. The liquid 16 in the vessel 10 can be a biological sample such as, human serum or haemolytic liquid. Other liquids such as, for example, analytes and the like may be used.

FIG. 2 shows a second embodiment of the apparatus, which differs from the first embodiment in that a polarizing beam splitter 25 can be inserted in the imaging optical path 22 instead of the polarizing filter 26.

Components in FIGS. 2-5 which can correspond to components in FIG. 1 are marked with the corresponding reference numbers. As to the explanation of those components reference is made to the above described first embodiment in FIG. 1. A polarizing beam splitter 25 in the second embodiment can act with the polarizing filter 18 to suppress light which can be directly reflected by the liquid surface. The polarizing beam splitter 25 can further provide a second imaging beam 32 that may be passed to a second image sensing device (not shown) or to another observing device.

The embodiment of FIG. 3 differs from the embodiment of FIG. 1 in that the position of the illumination device 2 and the position of the image sensing device 20 with the optical components 24, 28 have been exchanged so that in FIG. 3 the imaging optical path 22 can be folded by the minor 9 whereas the illuminating optical path 6 can be straight.

The embodiment according to FIG. 4 differs from the embodiment of FIG. 1 in that a common polarizing beam splitter 5 can be inserted in the illuminating optical path 6 and in the imaging optical path 22 whereas the polarizing filters 18, 26 can be omitted in the embodiment of FIG. 4.

In the embodiment according to FIG. 5, light emitting diodes 2 as illumination devices can be arranged equidistantly on a circle and in front of them a polarizing ring 18 can be provided in order to polarize the light emitted by the light diodes.

The vessel 10 can be positioned by the holder (not shown) at the predetermined location with its upper opening 12 exposed to the image sensing device 20 as shown FIGS. 1-5.

The illuminating light beam can be directed to the surface 14 of the liquid 16 and the image sensing device 20 can take an image of the liquid surface from the top of the vessel 10. The image data, such as, for example, pixel data with gray-scale and/or color information, can be transmitted to the data processing system for performing an automatic evaluation of that image on the basis of the image data whereas an image evaluation program can be used to identify foam specific areas in that image and to provide information about the presence or absence of foam specific areas in the image as a result of the image evaluation. The image evaluation program can apply applicable image processing algorithms in order to identify the border of the upper opening 12 and/or other features of the vessel 10 so that the type of vessel 10 can be determined by the data processing system. It can be useful to apply an algorithm which can perform a radial image calculation in order to assign the image data to radial coordinates or polar coordinates in cases of circular vessel openings 12. Then a best fit calculation of the vessel border to a sine and/or cosine curve can be possible. From the theoretical curve to sine and/or cosine function the center and radius of the vessel can be calculated and transferred to Cartesian coordinates. With the known radius of the vessel, the image part with the liquid sample (inner part of the vessel) can be extracted. The application of an operator for the detection of edges, such as, for example, the well-known Sobel-operator, to the image data or to corresponding data derived can be proposed in order to detect borders of foam specific areas in the image. Further, histogram calculations may be performed for that purpose. The image evaluation process can lead to information about the distribution of the foam on the liquid surface in the vessel 10, and that information can be processed for controlling the operation of an automated liquid pipetting system having a pipette for pipetting liquid from the vessel.

In the FIGS. 6a, 7a, 8a and FIGS. 6b, 7b and 8b, three different situations of foam occurrence in the vessel 10 and the influence of foam occurrence on a pipetting process are illustrated.

In FIG. 6a, the vessel is shown with a liquid 16 therein which has no foam on its upper surface 14. The pipette tip 35 can slightly dip into the liquid 16 such that a pipetting process may be performed without failure. FIG. 6b corresponds to the situation illustrated in FIG. 6a and shows an image taken with an image sensing device 20. The white circle 37 was sketched in in order to mark a central target area for the pipette tip 35.

In FIG. 7a, a relatively thick compact foam layer 39 rests on the liquid surface 14. The foam consists of a conglomerate of small bubbles with typical diameters between about 0.2 mm and 5 mm. Also bigger bubbles can be included. The pipette tip 35 in its predetermined immersion depth can end in the foam layer 39. When performing the pipette process, only foam may be sucked in the pipette and the pipetting result can be faulty. FIG. 7b is an image taken from the top of the vessel and shows the foam situation according to FIG. 7a.

FIG. 8a illustrates the situation where only an outer circular area of the liquid surface 14 is covered with foam 39 and the central region greater than the target region for the pipette tip 35 is free of foam. The tip 35 can dip into the target region of the liquid 16 and the pipetting process to be performed therewith will provide correct results. The foam situation shown in FIG. 8b corresponds to that illustrated in FIG. 8a.

An automatic decision can be made by the data processing system 30 whether the target area 37 on the liquid surface 14 is free of foam or covered with foam. This decision can be used to automatically control a liquid pipetting system. In the case of FIGS. 6a, 6b and 8a, 8b pipetting can be allowed whereas in the case of FIGS. 7a and 7b pipetting cannot be allowed.

It is to be noted that the method may be performed before and after a pipetting step in order to monitor the pipetting process. In a further embodiment, the method can be performed continuously also during the pipetting step.

The immersion depth of the pipette tip may be controlled by conventional controls.

Various variants can be possible. Illumination of the liquid surface may be performed by using optical fibres. The image sensing device may be adapted to provide information for a rough spectrum analysis of the sample in the vessel. According to one variant, dark field images can be taken and evaluated for foam detection. Also direct images (without the use of polarizing filters) may be taken and evaluated.

With reference to FIGS. 9-27, an example for determining foam specific areas to distinguish them from non-foam areas will be described as follows.

Example of Determining Foam Specific Areas

The following discussion is divided into two parts: the first part is concerned with how the vessel wall is detected and the second part discusses how the foam within the vessel is detected.

Vessel Detection

The measurement can comprise in general of two images, a first and a second image. FIG. 9 shows an example of a first image which serves to detect the vessel location and to evaluate the signal inside the vessel.

Transformation into Polar Coordinates

Figure 10:
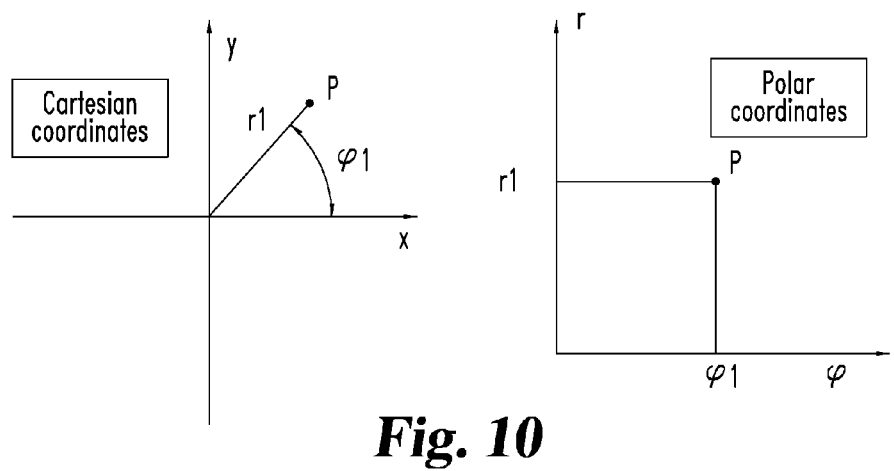
FIG. 10 illustrates the transformation from Cartesian coordinates to polar coordinates according to an embodiment of the present disclosure.

In a first step, the first image can be transformed from Cartesian coordinates to polar (or radial) coordinates as illustrated in FIG. 10. The mathematical background is given by the following formulas:

$$x = r \cdot \cos(\phi) \text{ and } y = r \cdot \sin(\phi)$$

Figure 11:
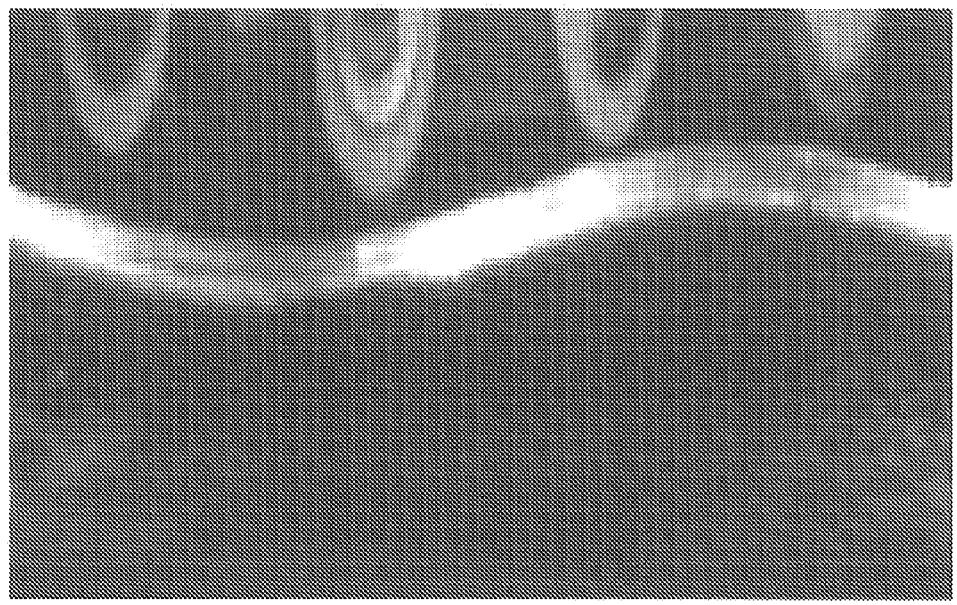
FIG. 11 illustrates the transformation of FIG. 9 from Cartesian to polar coordinates (radial image) according to an embodiment of the present disclosure.

As shown in FIG. 11, by transforming every pixel in the image and using the center of the image as the origin, a transformed (radial) image can be obtained. The horizontal axis in the image is now the angle $\phi$ (value between about 0° and 360°); the vertical axis is the radius.

Application of the Sobel Algorithm

The Sobel algorithm can be applied to the image to obtain a clear line of the vessel border in the radial image. Mathematically each pixel in the image can be convoluted with the following matrix operator:

$$\begin{pmatrix} -1 & -2 & -1 \\ 0 & 0 & 0 \\ 1 & 2 & 2 \end{pmatrix}$$

Figure 12:
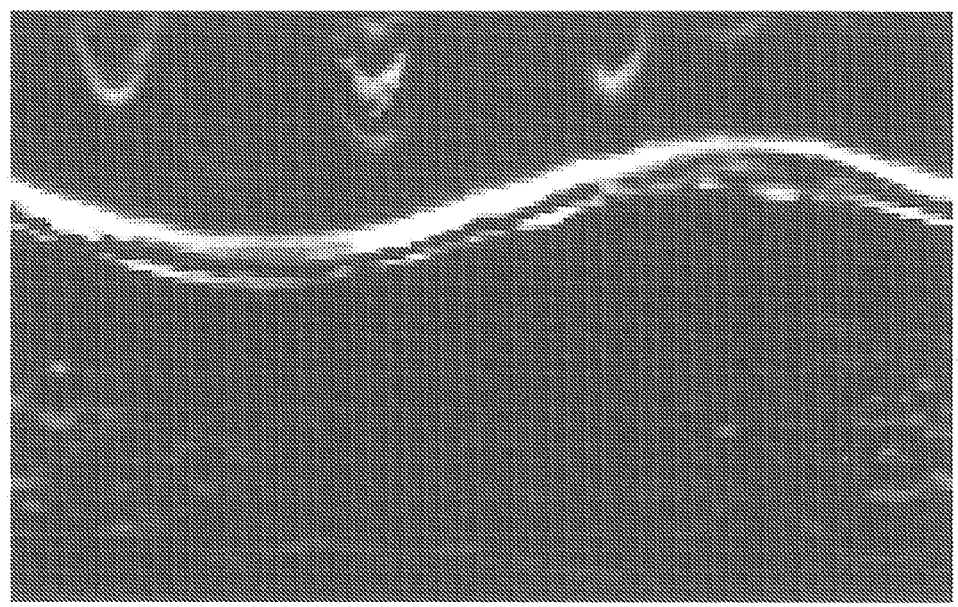
FIG. 12 illustrates the result of the Sobel operator applied to the radial image in FIG. 11 according to an embodiment of the present disclosure.
Figure 13:
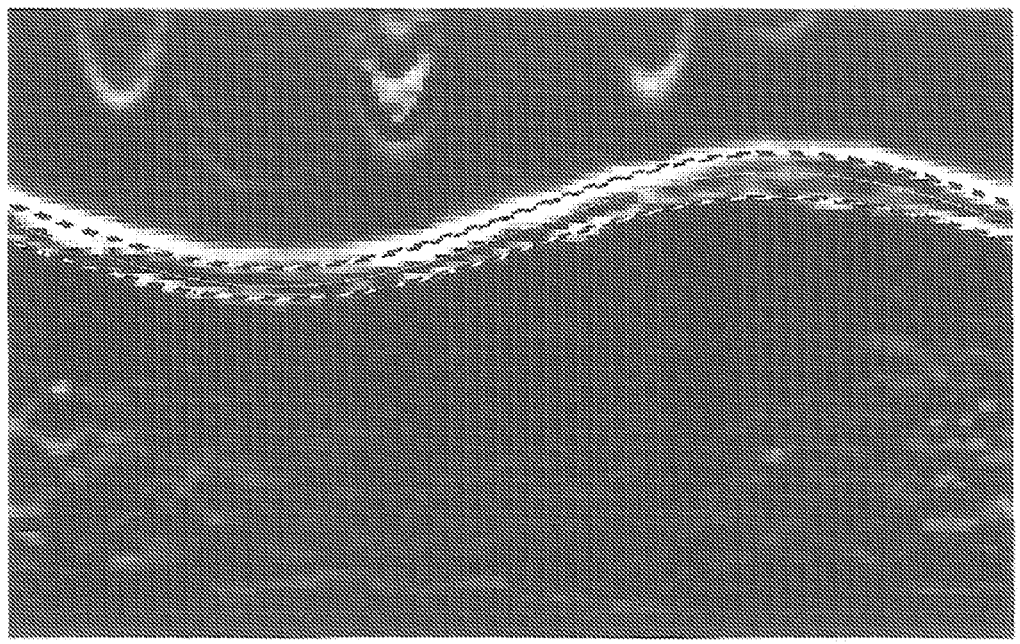
FIG. 13 illustrates the sine curves determined with the Hough transformation that describe the vessel border according to an embodiment of the present disclosure.

This operator can amplify horizontal lines which can have a low signal in the upper parts of the image and a high signal in the lower parts. The result is shown in FIG. 12. Any other operator which amplifies the lines can also be used.

Hough Transformation

For finding the upper sinusoidal bright light, a Hough transformation can be used: Image pixels can be added up along sinusoidal curves which can be described by the following formula:

$$r = a + b \sin(\phi + c)$$

The parameters a, b and c can be varied and the sum of the signals of the image pixels along the sinusoidal curve can be added up. This can give signals as a function of a, b and c, which contain local maxima. For example, let $a_1$, $b_1$ and $c_1$ the parameters where the maximum signal can be found. In this case, it can be most likely that the sine curve describes the border of the vessel. An example of the found sine curves describing the vessel border, is given in FIG. 13.

The parameter $a_1$ can describe the radius of the vessel; $b_1$ can describe how much the vessel is decentred, while $c_1$ can give information about the direction of the vessel decentration. The sum of the signal obtained on the sine curve can be a quality parameter for the total strength of the line and can be used if several sine curves with similar sum signals have been found. If the signal is similar for two or more sine curves, the vessel can be described by the curve with the maximum value for a, i.e. the maximum radius.

The vessel circle in the original image can be simply found by calculating the radius and decentre of the circle from the parameters in the sine curve. An example of the vessel wall found by the algorithm described above, is depicted in FIG. 14.

Figure 14:
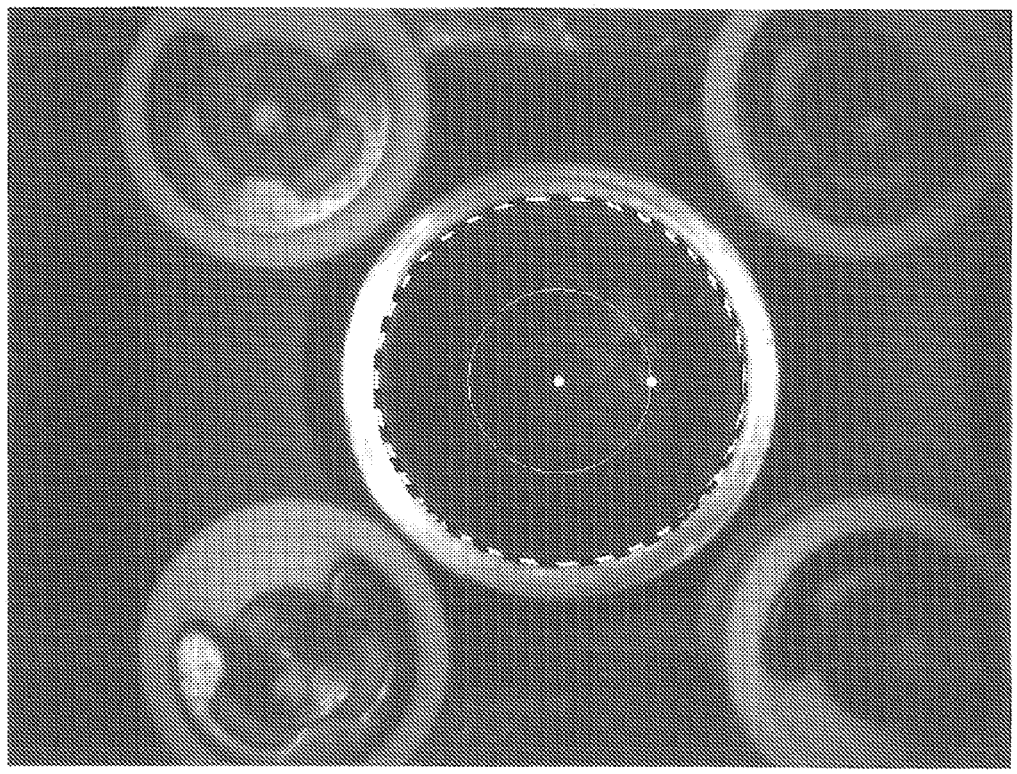
FIG. 14 illustrates the inner vessel circumference found by the combination of the Sobel and Hough algorithm according to an embodiment of the present disclosure.

In FIG. 14, the vessel thickness has already been subtracted and the result is depicted by the dashed (white and black) circle.

Foam Detection

Prior to the foam detection, the mean signal $S_m$ inside the dashed (white and black) circle (inner circle of the vessel) in FIG. 14 can be calculated and compared with a desired value $S_d$. This can help to adjust for example the camera gain to increase or decrease the brightness to the desired value. Other methods to adjust the brightness of the image can be
  the reduction or increase of the exposure time.
  the reduction or increase of the light intensity (which is used for the illumination of the sample).
  the reduction or increase of the pulse duration, if light from a strobe is used for the illumination of the sample).

Figure 15:
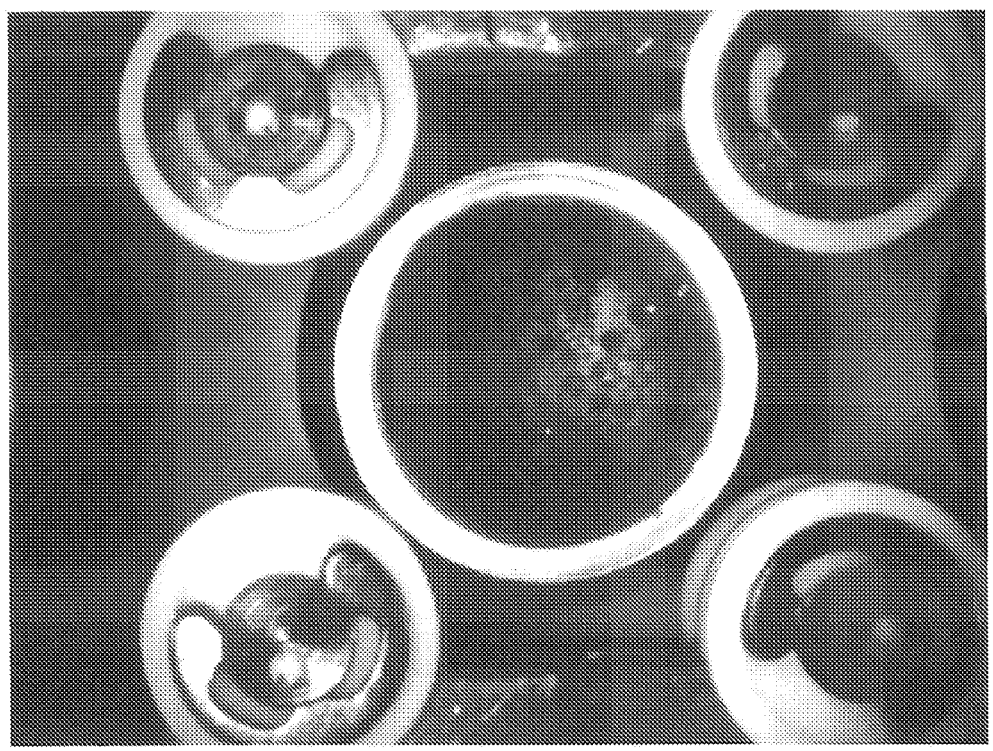
FIG. 15 illustrates an improved image of FIG. 9, according to the applied image processing algorithm according to an embodiment of the present disclosure.
Figure 16:
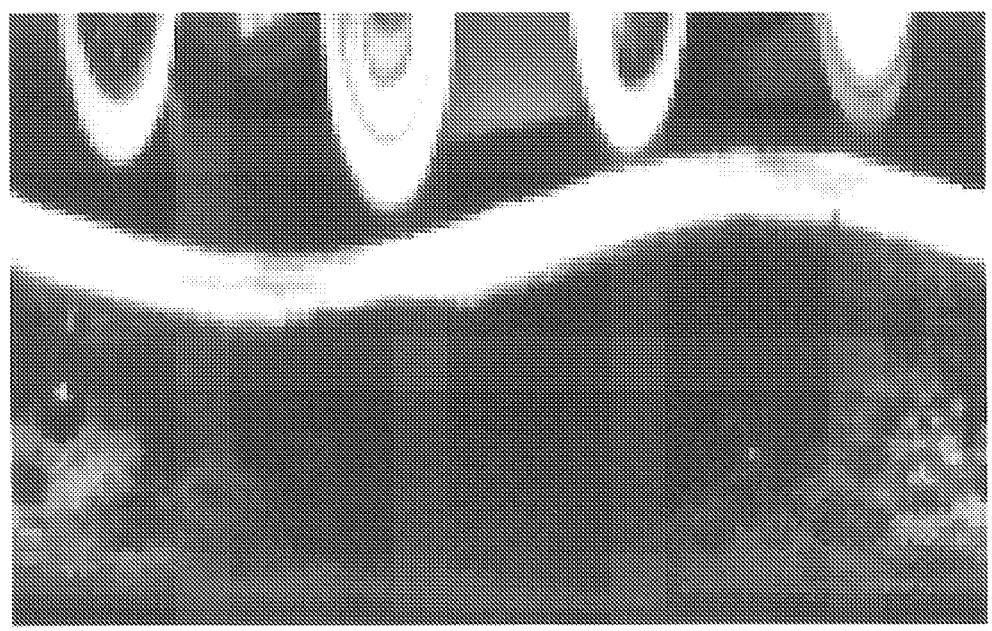
FIG. 16 illustrates the transformation of FIG. 15 from Cartesian to polar coordinates according to an embodiment of the present disclosure.

After the adjustment of e.g., the light intensity, a second image of the sample can be recorded. FIG. 15 shows an image with adapted intensity. The vessel position and the inner part of the vessel can be obtained again by the procedures described above or can be taken from the first image if there has been no movement during the capture of the two images.

Transformation into Polar Coordinates

The transformation of FIG. 15 into polar coordinates as described above is shown in FIG. 16 which shows a radial image of the foam image.

The vessel position and radius can be found in the same way as described above. From the amplitude and phase of the sine curve, the displacement of the vessel from the center can be calculated and the center of the vessel can be deduced.

Extraction of the Foam Part in the Radial Image

Figure 17:
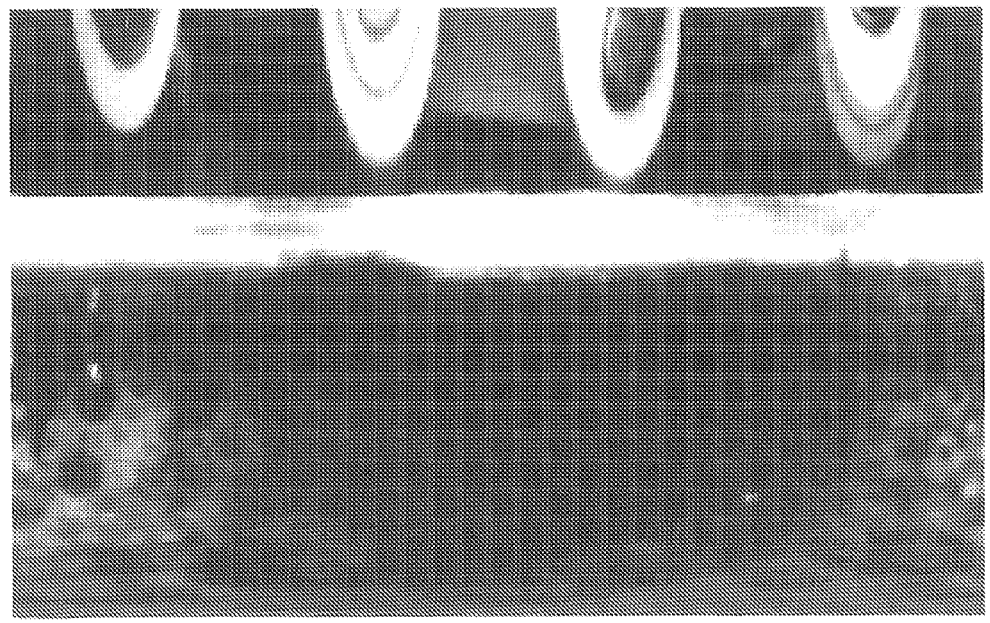
FIG. 17 illustrates FIG. 15 when the centre of the vessel is equivalent to the center of the image according to an embodiment of the present disclosure.

With the new center the radial image can be recalculated. The resulting radial image with the center of the vessel is shown in FIG. 17.

Figure 18:
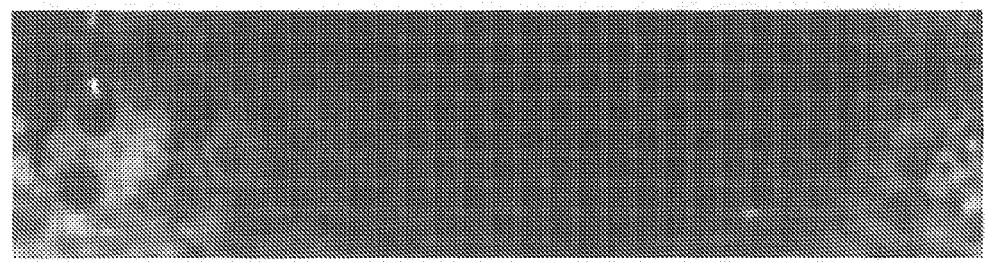
FIG. 18 illustrates the extracted inner vessel (foam) area of FIG. 17 according to an embodiment of the present disclosure.

The vessel border can now be a straight line. For the following considerations, it can be assumed that only an annular region of the liquid surface around the center of the vessel is of interest for deciding about the presence of foam. The annular region may have for example, an inner radius of about 1.5 mm and an outer radius of about 5 mm such that the outer diameter of the annular region can be approximately 10 mm. Experiments showed that in a center region with a diameter of about 3 mm no foam usually can occur if there is no foam in the above mentioned annular region. An example of an extracted image of such an annular region is shown in FIG. 18. A larger range may not be necessary since in the present example we are only interested whether foam exists within a diameter of about 6 mm. Different further algorithms can lead to the decision whether there has been foam within a circle of such a diameter or not. In the following, the main three algorithms are described.

Histogram Evaluation of the Radial Image

In a first step, the extracted foam image can be convoluted with two different matrix operators (Sobel operators) described by two matrices:

$$\begin{pmatrix} -1 & -2 & -1 \\ 0 & 0 & 0 \\ 1 & 2 & 2 \end{pmatrix} \text{ and } \begin{pmatrix} -1 & 0 & 1 \\ -2 & 0 & 2 \\ -1 & 0 & 1 \end{pmatrix}$$

The process can be similar to the one described above. The algorithm can find steep changes in pixel brightness in the vertical and horizontal direction. Negative and positive changes in intensity can be observed. If a negative change is calculated, the absolute amount can be taken.

Figure 19:
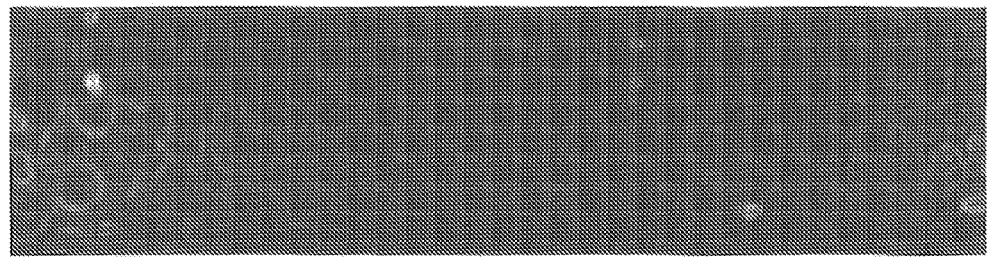
FIG. 19 illustrates FIG. 18 converted using the Sobel operators according to an embodiment of the present disclosure.

In this way, two images can be obtained for the two matrices (applied to the same radial image). The image obtained with the first matrix can emphasize steps in the horizontal direction whereas the other matrix can give more information about steps in the vertical direction. The average of the two images can show areas where steps in any direction can occur. The final calculated (or converted) radial image with Sobel operators for the example of FIG. 18 is shown in FIG. 19. In the image, it can be already clearly seen, that there can be foam especially on the right and left side of the image. The foam can become even more evident when an additional algorithm is applied: A histogram algorithm where for each pixel in the image a histogram around the pixel is calculated.

Figure 20:
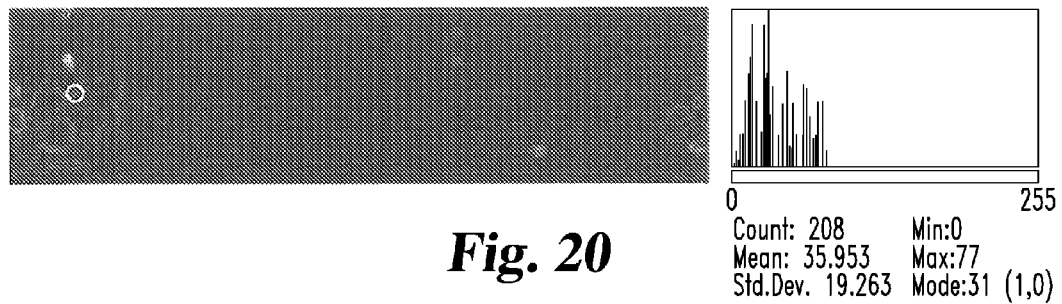
FIG. 20 illustrates a histogram (right) for an inner vessel area (left) with large contrast (foam area) according to an embodiment of the present disclosure.

To explain the algorithm, the following two examples are presented:

FIG. 20 shows a histogram for structures with large contrast. The histogram inside the white circle, where the intensity changes can be large, has been calculated and can leads to a standard deviation of larger than about 19.

Figure 21:
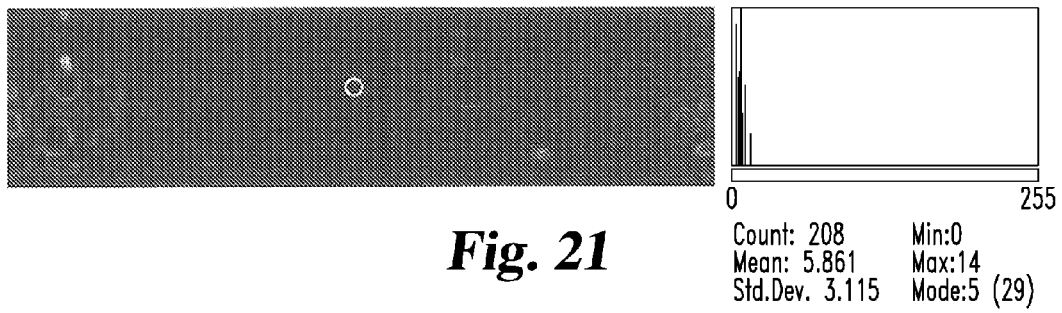
FIG. 21 illustrates a histogram (right) for an inner vessel area (left) with small contrast (non-foam area) according to an embodiment of the present disclosure.
Figure 22:
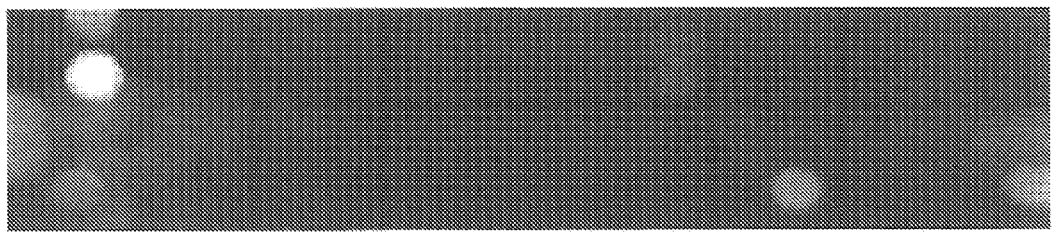
FIG. 22 illustrates an image that displays histogram standard deviations according to an embodiment of the present disclosure.

FIG. 21 shows a histogram for structures with small contrast. FIG. 21 illustrates that in regions with smaller changes of the intensity, the histogram can be much narrower than in FIG. 20 (standard deviation can now be about 3).

The example illustrates that the standard deviation can be a suitable approach to detect foam regions. Using the calculation for all pixels in the image and displaying the standard deviation in a new image, FIG. 22 can be obtained which shows an image with the display of the histogram standard deviation.

At least on the right and left hand side, it can become evident that there can be a lot of foam.

FFT Evaluation of the Radial Image

Although about 80% to 90% of the foam images can be detected by the method above (histogram image calculation), an additional algorithm can help to distinguish between images with foam and without foam. The algorithm can start with the radial extracted image such as, for example, as depicted in FIG. 18. For each pixel, neighboring horizontal pixels can be used and the Fourier coefficients can be calculated. In particular, 32 horizontal pixels can be used in most cases to calculate the Fourier coefficients of the center pixel. Mathematically speaking S(i,j) shall be the intensity of the pixel at the horizontal position i and vertical position j. For the calculation with 32 pixel in horizontal direction, the signals between the horizontal positions at i−15 to i+16 can be taken and approximated by the Fourier transform:

$$\tilde{S}(i, j) = S_0 + \sum_{k=1}^{15} A_k(i, j) \cdot \sin\left(\frac{2 \cdot \pi}{k} \cdot i\right) + \sum_{k=1}^{15} B_k(i, j) \cdot \cos\left(\frac{2 \cdot \pi}{k} \cdot i\right)$$

The higher the coefficients $A_k$ and $B_k$ for large k, the more likely foam can be found in this area, since at these positions changes of the pixel intensity over a small distance can be expected for foam. For simplification, coefficients with k larger than 2 can be taken and the square sum can be calculated for every pixel in the image:

$$\frac{\sum_{k=3}^{15} A_k(i, j)^2 + B_k(i, j)^2}{S_0}$$

Calculating this signal for every image pixel can yield the Fourier transform converted image shown in FIG. 23. The maximum FFT signal for a radius below about 4 mm can be taken as a indication for the foam, that is, the larger the value, the more likely foam can be present. Other foam images converted by Fourier transformation can even show more clearly that foam may be present. This is illustrated in FIG. 24, where the radial Fourier transformed image on the right hand side is shown for the foam imagine on the left hand side. Statistic evaluation of many samples (about 1000) showed that the Fourier transformation can be very helpful to further increase the detection probability of foam to a value higher than about 95%.

Ring Detection

Figure 25:
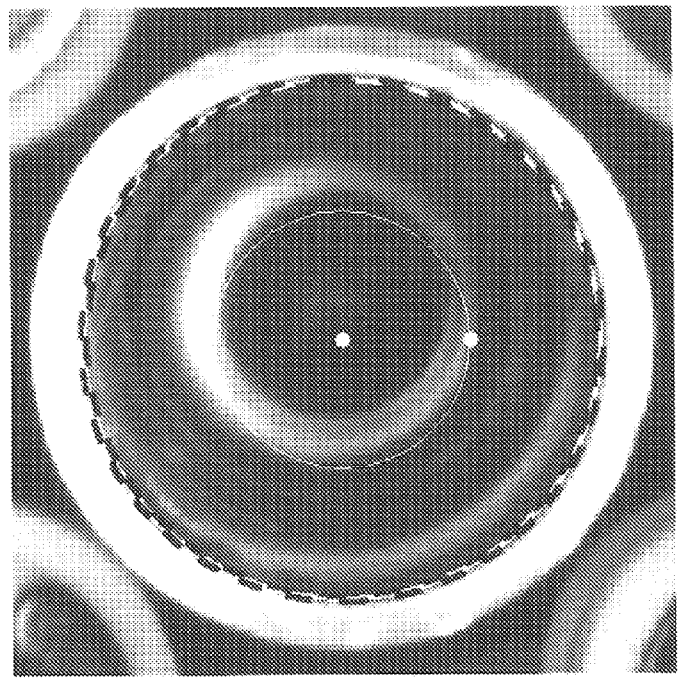
FIG. 25 illustrates a foam image with a bright ring according to an embodiment of the present disclosure.

The two algorithms described above can be in most cases sufficient to separate foam images from non-foam images. However, in some cases, artifacts can occur during the capture of foam images. The most severe effect can be caused by reflection from the bottom of the vessel which can be observed as bright rings. An example of a foam image with a bright ring is shown in FIG. 25.

Figure 26:
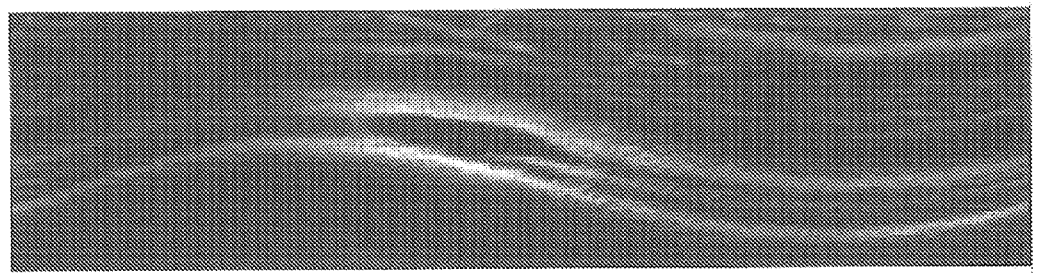
FIG. 26 illustrates the result of the application of the Sobel operator to the radial image of FIG. 25 according to an embodiment of the present disclosure.
Figure 27:
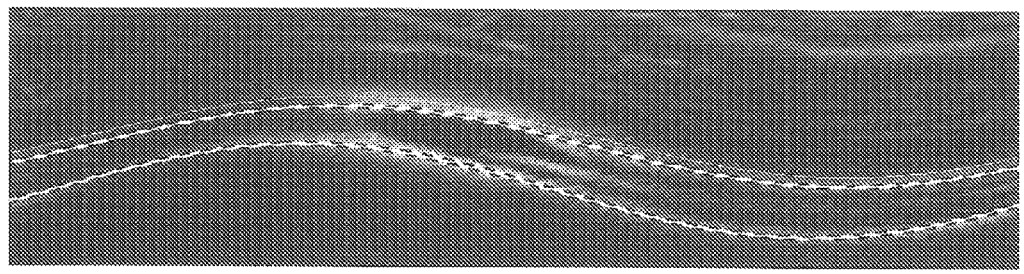
FIG. 27 illustrates the bright rings as detected by the Hough transformation according to an embodiment of the present disclosure.

Calculation of the radial image (similar to FIG. 16 and FIG. 17), extraction of the foam image (similar to FIG. 18) and application of the Sobel operator (similar to FIG. 19) can lead to the radial Sobel image (with rings) shown in FIG. 26. Using the Hough algorithm (finding sinusoidal curves in the image) described above, the curves can be clearly detected. The bright rings detected by Hough transformation are shown in FIG. 27. The presence of the rings can be an indication that the bright signals can be coming from the vessel background and not from foam. The sample can be therefore characterized as being without foam.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A method for detecting foam on a liquid surface in a vessel, the method comprising:
    providing a vessel having an upper opening surrounded by a border and containing an amount of a liquid;
    taking at least one image from a region suspected to contain foam in the vessel by using an image sensing device that provides corresponding image data, wherein the at least one image is taken from the top of the vessel through the open upper opening onto the liquid surface and wherein the border of the vessel is included in the image;
    performing an automatic evaluation of the image on the basis of the image data by a data processing system using an image evaluation program, wherein the image evaluation program identifies foam areas and non-foam areas in the at least one image and provides information about the presence or absence of foam areas in the at least one image as a result of the image evaluation; and
    detecting the border of the vessel and the center of the opening by application of image evaluation algorithms.

2. The method according to claim 1, wherein the vessel is tube-shaped.

3. The method according to claim 1, wherein when taking the at least one image, the liquid surface is illuminated from the top of the vessel and the image is taken through a polarizing filter in order to suppress light which is reflected directly from the liquid surface.

4. The method according to claim 3, wherein the illumination light is linearly polarized and wherein the polarizing filter, through which the image is taken, transmits light that is polarized perpendicular with regard to the polarization direction of the illumination light.

5. The method according to claim 1, wherein when taking the at least one image, a series of corresponding images of the liquid surface is taken by using the image sensing device and wherein the data of corresponding image pixels are averaged to provide a respective mean value of each pixel for further data processing when performing the automatic evaluation.

6. The method according to claim 1, wherein a radial image is calculated in which the image points or pixels being assigned to radial coordinates or polar coordinates and wherein a best fit calculation of the vessel opening border is performed with a best fit to a curve which is close to a sine and/or cosine curve.

7. The method according claim 1, wherein an operator for the detection of edges is applied to at least a part of the image data or to corresponding data derived therefrom, in order to detect borders of foam specific areas in the image.

8. The method according claim 7, wherein the operator is a Sobel-Operator.

9. The method according to claim 1, wherein the detection is at least a predetermined central region of the image part surrounded by the border of the opening and is substantially free of foam specific areas.

10. An apparatus for detecting foam on a liquid surface in a vessel having an upper opening surrounded by a border and containing an amount of a liquid, the apparatus comprising:
    a holder for positioning the vessel with its opening at the top at a predetermined location;
    an illumination device for illuminating the liquid surface in the vessel when the vessel is positioned at the predetermined location;
    an image sensing device for taking at least one image from a region suspected to contain foam in the vessel when the vessel is positioned at the predetermined location and for providing corresponding image data, wherein the image sensing device is positioned and adapted to take the at least one image, including the border of the vessel from the top of the vessel through the open upper opening onto the liquid surface; and
    a data processing system for performing an automatic evaluation of the at least one image on the basis of the image data and for using an image evaluation program, wherein the image evaluation program of the data processing system detects the border of the vessel and the center of the opening, identifies foam areas and non-foam areas in the image and provides information about the presence or absence of foam areas in the image as a result of the image evaluation.

11. The apparatus according to claim 10, wherein the illumination device includes at least one light source and at least one reflecting device for reflecting light of the light source such that the reflected light will enter the opening of the vessel to illuminate the liquid surface in the vessel from above.

12. The apparatus according to claim 10, wherein at least one optical imaging lens is arranged in front of the image sensing device and wherein an iris is positioned in front of the lens.

13. The apparatus according to claim 10, wherein a polarizing filter is arranged in the imaging optical path between the vessel and the image sensing device.

14. The apparatus according to claim 13, wherein the polarizing filter is arranged in the illuminating optical path between the light source and the vessel, the direction of polarization of that polarizing filter is perpendicular to the direction of polarization of the polarizing filter arranged in the imaging optical path.

15. The apparatus according to claim 10, wherein the apparatus is a part of an automatic liquid pipetting system which comprises at least one pipette that operates between the image sensing device and the vessel at its predetermined location to suck liquid from the vessel.

16. The apparatus according to claim 10, wherein the apparatus is a part of an automatic liquid pipetting system which comprises at least one pipette and wherein the image sensor device is attached to the pipettor.

17. The apparatus according to claim 16, wherein the automatic liquid pipetting system has a controller that communicates with the data processing system, the controller controls the pipette in dependence of information provided by the data processing system about the presence or absence of foam specific areas in the respective vessel.

* * * * *